United States Patent
Marra et al.

(10) Patent No.: US 11,298,728 B2
(45) Date of Patent: Apr. 12, 2022

(54) METHOD AND SYSTEM OF MONITORING THE CLEANING OF HOSPITAL ENVIRONMENTS

(71) Applicants: Sociedade Beneficente Israelita Brasileira Hospital Albert Einstein, São Paulo (BR); I-HealthSys Produtos Médicos Ltda—ME, São Carlos (BR)

(72) Inventors: Alexandre Rodrigues Marra, São Paulo (BR); Marcelo Prado, São Carlos (BR); Renaldo Massini Junior, São Carlos (BR); Alvaro Costa Neto, São Carlos (BR)

(73) Assignees: Sociedade Beneficente Israelita Brasileira Hospital Albert Einstein, São Paulo (BR); I-HealthSys Produtos Médicos Ltda—ME, São Carlos (BR)

( * ) Notice: Subject to any disclaimer, the term of this patent is extended or adjusted under 35 U.S.C. 154(b) by 399 days.

(21) Appl. No.: 15/968,103

(22) Filed: May 1, 2018

(65) Prior Publication Data
US 2019/0299259 A1    Oct. 3, 2019

(51) Int. Cl.
*B08B 7/00* (2006.01)
*G08B 21/24* (2006.01)

(52) U.S. Cl.
CPC ............ *B08B 7/0057* (2013.01); *G08B 21/24* (2013.01)

(58) Field of Classification Search
CPC ....... B08B 7/0057; B08B 13/00; G08B 21/24; G08B 21/245; G06Q 10/0631; G06Q 10/0639; G06Q 10/063114; G06Q 10/30; G16H 40/20; G02B 27/017; G02B 2027/0178; Y02W 90/00
See application file for complete search history.

(56) References Cited

U.S. PATENT DOCUMENTS

| | | | | |
|---|---|---|---|---|
| 9,922,533 | B2* | 3/2018 | Hayes | A61L 2/26 |
| 10,529,218 | B2* | 1/2020 | Marra | G08B 21/245 |
| 2006/0223731 | A1* | 10/2006 | Carling | C11D 3/40 |
| | | | | 510/156 |
| 2009/0195385 | A1* | 8/2009 | Huang | G16H 40/20 |
| | | | | 340/572.1 |
| 2009/0276239 | A1* | 11/2009 | Swart | G06Q 10/06375 |
| | | | | 705/2 |
| 2010/0319729 | A1* | 12/2010 | Jensen | B08B 3/00 |
| | | | | 134/18 |
| 2011/0057799 | A1* | 3/2011 | Taneff | G08B 21/245 |
| | | | | 340/573.1 |

(Continued)

*Primary Examiner* — Alexander Markoff
(74) *Attorney, Agent, or Firm* — Patterson + Sheridan, LLP

(57) ABSTRACT

There is described a method of monitoring the cleaning of hospital environments, the hospital environment (1) comprising at least an item (2, 2a, 2b, 2c, 2d, 2e, 2f, 2g, 2h, 2i, 2j) disposed inside thereof, wherein the method comprises the steps of: generating a statement of events (5,5',5") of the hospital environment (1), the statement of events (5,5',5") related to the occurrence of at least a touch between at least a passer-by (3,3',3",30) of the hospital environment (1) with one of the items (2, 2a, 2b, 2c, 2d, 2e, 2f, 2g, 2h, 2i, 2j) disposed in the hospital environment (1), and performing the cleaning action of the hospital environment (1) based on the statement of events (5,5',5") generated. A system of monitoring the cleaning of hospital environments is also described.

11 Claims, 10 Drawing Sheets

(56) References Cited

U.S. PATENT DOCUMENTS

Figure 1:
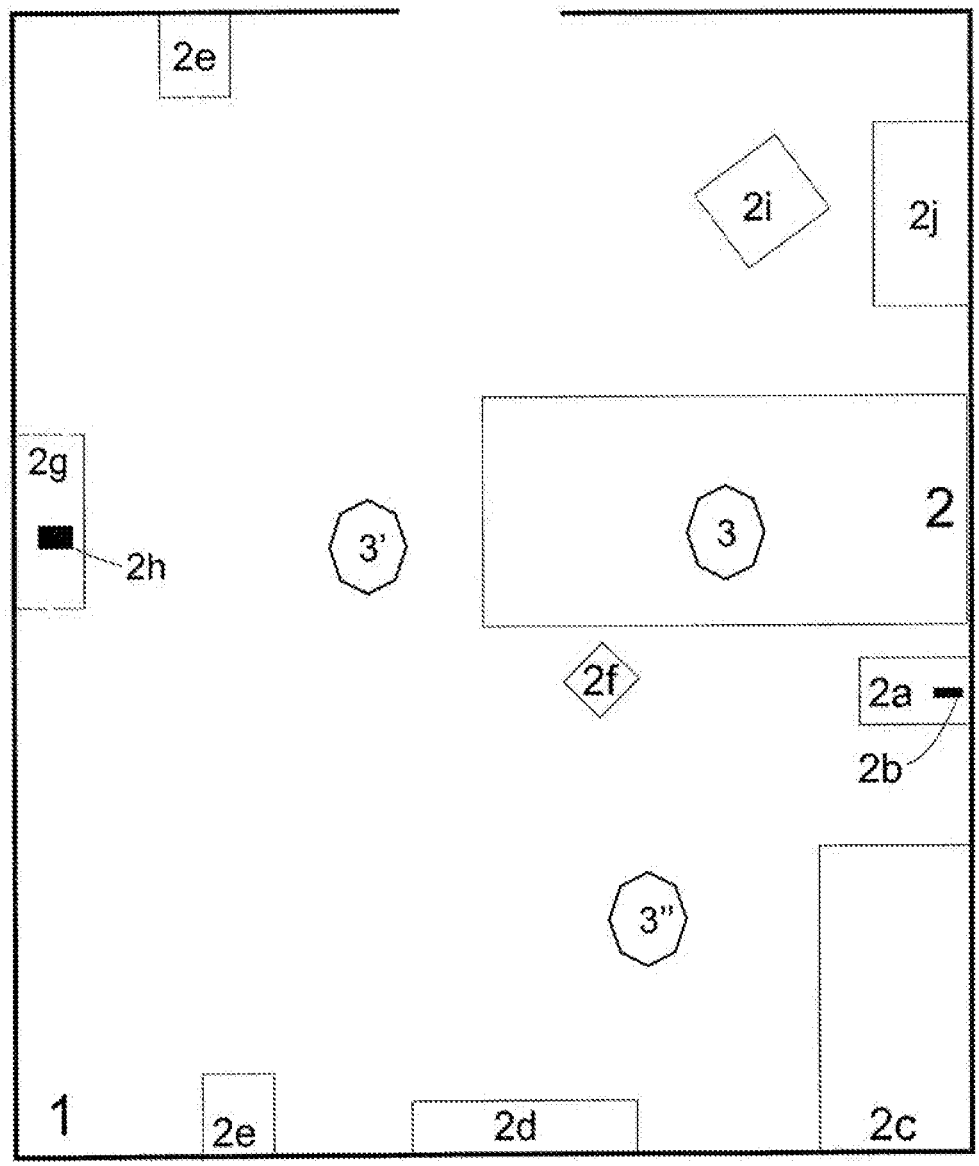

| | | | |
|---|---|---|---|
| 2011/0163870 A1* | 7/2011 | Snodgrass | A61B 5/1122 340/539.11 |
| 2012/0173274 A1* | 7/2012 | Rensvold | G08B 21/245 705/2 |
| 2012/0194338 A1* | 8/2012 | Snodgrass | G08B 21/245 340/539.12 |
| 2012/0268277 A1* | 10/2012 | Best | G08B 21/245 340/573.1 |
| 2013/0126760 A1* | 5/2013 | Klein | A61L 2/10 250/492.1 |
| 2013/0127615 A1* | 5/2013 | Snodgrass | G06F 21/35 340/539.13 |
| 2013/0285814 A1* | 10/2013 | Snodgrass | G08B 21/245 340/573.1 |
| 2014/0030144 A1* | 1/2014 | Krosney | B01D 53/007 422/4 |
| 2014/0070950 A1* | 3/2014 | Snodgrass | G16H 40/20 340/573.5 |
| 2014/0108039 A1* | 4/2014 | Rensvold | G08B 21/245 705/2 |
| 2014/0333744 A1* | 11/2014 | Baym | G08B 21/245 348/77 |
| 2014/0358573 A1* | 12/2014 | Balinski | G16H 40/63 705/2 |
| 2015/0078960 A1* | 3/2015 | Krosney | A61L 9/20 422/4 |
| 2016/0038624 A1* | 2/2016 | Krosney | A61L 9/20 422/121 |
| 2016/0121012 A1* | 5/2016 | Krosney | A61L 9/20 422/105 |
| 2016/0125723 A1* | 5/2016 | Marra | G08B 21/245 340/573.1 |
| 2016/0148485 A1* | 5/2016 | Hayes | G08B 21/245 340/665 |
| 2016/0171179 A1* | 6/2016 | Donofrio | G16H 15/00 705/2 |
| 2016/0247381 A1* | 8/2016 | Rensvold | G16H 40/20 |
| 2017/0232125 A1* | 8/2017 | Carling | A61L 2/18 434/219 |
| 2017/0270267 A1* | 9/2017 | Muller-Wende | G06Q 50/22 |
| 2018/0144609 A1* | 5/2018 | Marra | G08B 5/36 |
| 2018/0264391 A1* | 9/2018 | Kirschman | B01D 46/448 |
| 2018/0308339 A1* | 10/2018 | Marra | G08B 5/36 |
| 2019/0080797 A1* | 3/2019 | Colburn | G06K 7/10366 |
| 2019/0102520 A1* | 4/2019 | Marra | G16H 70/60 |
| 2019/0331701 A1* | 10/2019 | Polley | G01N 35/0099 |

* cited by examiner

Statement of Events

Medical Professional

| Item | Number of touches |
|---|---|
| Bed | 3 |
| Support bench | 5 |
| Telephone | 0 |
| Visitor's bed | 0 |
| Windows | 0 |
| Dispensers | 3 |
| Infusion pump | 1 |
| Bench | 1 |
| TV set | 0 |
| Armchair | 0 |
| Nurse's bench | 1 |

FIG. 2

5' Consolidated statement of events

| Item | Number of touches |
|---|---|
| Bed | 6 |
| Support bench | 8 |
| Telephone | 2 |
| Visitor's bed | 2 |
| Windows | 4 |
| Dispensers | 15 |
| Infusion pump | 2 |
| Bench | 5 |
| Tv set | 4 |
| Armchair | 3 |
| Nurse's bench | 5 |

FIG. 3

Detailed Statement of Events

Medical Professional

| Item | Total touches: 3 |
|---|---|
| Bed | Episode 1:<br>15/01/2019 -> 14:44  — 5a<br>Duration: 2 seconds<br><br>Episode 2:<br>17/01/2019 -> 7:20  — 5b<br>Duration: 0,3 second<br><br>Episode 3:<br>17/01/2019 -> 11:14  — 5c<br>Duration: 4 seconds |

| Item | Total touches: 3 |
|---|---|
| Dispenser | Episode 1:<br>15/01/2019 -> 10:33  — 5a<br>Duration: 2 seconds<br><br>Episode 2:<br>17/01/2019 -> 7:10  — 5b<br>Duration: 1 second<br><br>Episode 3:<br>17/01/2019 -> 11:11  — 5c<br>Duration: 2 seconds |

FIG. 4

Statement of Events and Index of Dirtiness

| Item | Number of touches (5) | Index of Dirtiness (6) |
|---|---|---|
| Bed | 3 | 70% |
| Support Bench | 5 | 75% |
| Telephone | 2 | 60% |
| Visitor's bed | 0 | 0% |
| Windows | 0 | 0% |
| Dispensers | 3 | 70% |
| Infusion pump | 1 | 50% |
| Bench | 1 | 40% |
| TV set | 0 | 20% |
| Armchair | 0 | 0% |
| Nurse's bench | 1 | 35% |

FIG. 5

METHOD AND SYSTEM OF MONITORING THE CLEANING OF HOSPITAL ENVIRONMENTS

The present invention refers to a method and a system of monitoring the cleaning of hospital environments. Thus, the present invention addresses a methodology and a system capable of evaluating whether the cleaning performed in hospital environments was properly performed considering certain events occurring in the hospital environment. More specifically, the teachings of the present invention use as basis the detection of so-called 'hot spots' (points where a greater quantity of touches occurs) and the indication thereof, in real time, for the cleaning team.

DESCRIPTION OF THE STATE OF THE ART

In hospital environments, there is a constant search for procedures that reduce the proliferation of virus and bacteria and that consequently also prevent the occurrence of infections.

A prominent feature of these procedures is the investment made by hospital management in monitoring the practice of hand sanitization. Thus, dispensers mostly comprising alcohol gel are disposed at various points of a hospital so that patients, visitors, collaborators and health professionals are able to sanitize their hands several times during the day.

Moreover, sensors are disposed throughout the hospital and in specific (bedroom) environments for monitoring whether the hygiene practice performed by a certain professional and/or visitor is deemed adequate for a certain situation.

In the same way that infections can be caused due to inadequate hand sanitization, they may also occur due to ineffective cleaning of the hospital environment per se and of the elements (items) disposed inside the environment.

Considering a hospital bed (room) occupied by a certain patient, it is essential that said bed be cleaned daily so that the chance of infections is reduced. Said daily cleaning is commonly addressed as concurrent cleaning.

Similarly, when said patient is discharged, it is vital to clean the bed so that it may accommodate the next patient, upholding due sanitization standards. This type of cleaning is referred to as terminal cleaning.

It so happens that the management in charge of the hygiene and cleaning of the hospital errs by providing due monitoring of the cleaning performed in the bedroom (be it concurrent or terminal). In fact, in the majority of cases there is no type of supervision of the cleaning process performed in the hospital environment.

Such cleaning processes are commonly performed by outsourced professionals who follow a specific protocol of points to be cleaned, for example, handles, telephones, tables, medical equipment, beds, among others.

Additionally, the cleaning of certain points is performed starting with visual aspects of the environment, for example, when a spot of blood is seen on the floor or a splash of a certain medicine on the furniture of the hospital room.

So the absence of supervision and of any type of monitoring is highly detrimental for the cleaning of the hospital environment. In some cases, the arrangement of video cameras in certain environments showed that, in extreme cases, professionals assigned to carry out terminal cleaning remain inside the room, but without effectively cleaning it.

Further, in hospital environments where a minimum time period is required for performing the terminal cleaning (for example, 30 minutes), in certain cases the professional effectively cleans the environment for just 5 minutes, using the remaining time, for example, spent on the cellphone.

Thus, it is imperative to consider new procedures designed to increase efficiency and monitor the cleaning practices in hospital environments, with a view to reducing the chance of occurrence of infections.

In this sense, the present invention is designed to overcome the problems existing in the state of the art through the provision of method and system of monitoring the cleaning of hospital environments, said method and system guaranteeing the efficiency of the cleaning to be performed and without the need for a third party (in loco) to accompany the professional in charge of cleaning.

More specifically, and contrary to the teachings of the state of the art in which the cleaning follows a same protocol for all bedrooms of a hospital, the present invention addresses a methodology and a system in which the cleaning of each environment (bedroom) is performed considering the most recent events occurring in that bedroom, in which said events are related to a potential chance of proliferation of bacteria.

Thus, events occurring in a certain bedroom can be related to the chance of proliferation of bacteria, also generating an index (ranking) relating to which points of the hospital environment are dirtier considering the events occurring, whereby enabling the cleaning team to act with greater emphasis and care on such points.

Further, and differently to that disclosed in the state of the art where the cleaning is performed without any type of supervision, the present invention proposes a methodology and a system that make use of an indicating element associated to the cleaning team, said indicating element acting as a supervisor for the cleaning carried out, indicating to the professional the next point to be cleaned considering the specific events of that bedroom and issuing warnings if the cleaning does not occur at a point which should have been cleaned.

Further, the use of the indicating element enables hospital management to monitor, in real time and remotely, the cleaning in progress for the hospital environment, detecting and monitoring whether the cleaning was performed efficiently considering the events occurring previously for the hospital environment in question.

Accordingly, a method and a system of monitoring the cleaning of hospital environments is addressed, designed for improved efficiency of the cleaning practices of the bedroom of a hospital, whereby enhancing care for patients and reducing the chance of proliferation of bacteria and the occurrence of infections. The teachings of the present invention use as basis the detection of so-called 'hot spots' (points where a greater quantity of touches occurred) and the indication thereof, in real time, for the cleaning team.

So the system and method are entirely automated, with the detection of points where a greater quantity of touches occurred ('hot spots') and the indication thereof for the professional assigned to carry out the cleaning.

OBJECTIVES OF THE INVENTION

The objective of the present invention is the provision of a method of monitoring the cleaning of hospital environments.

An additional objective of the present invention consists in providing a method of monitoring the cleaning of hospital environments wherein the cleaning of the hospital environment is performed considering specific events (episodes) of a certain environment to be cleaned.

A third objective of the present invention consists in providing a method of monitoring the cleaning of hospital environments wherein the cleaning of the hospital environment is performed based on touch events occurring between a passer-by of the hospital environment and a certain item disposed in the environment.

A further objective of present invention is to propose a method of monitoring the cleaning of hospital environments wherein the touch events occurring in a certain environment are used to generate an index relating to the degree of dirtiness of the items disposed in the hospital environment.

An additional objective of the present invention consists of proposing a method of monitoring the cleaning of hospital environments that makes use of an indicating element associated to the team in charge of cleaning the hospital environment.

The present invention also has the objective of proposing that the cleaning action performed in the bedroom can be monitored, in real time and remotely, by the management of the hospital environment.

An additional objective of the present invention consists of proposing an arrangement of the indicating element as an element endowed with an enhanced reality interface.

An additional objective of the present invention refers to the proposed arrangement of the indicating element as a mobile device, such as a cellphone, tablet or smart glasses.

The present invention also has the objective of providing a system of monitoring the cleaning of hospital environments in harmony with the proposed methodology.

BRIEF DESCRIPTION OF THE INVENTION

The objectives of the present invention are achieved by a method of monitoring the cleaning of hospital environments, the hospital environment comprising at least an item disposed inside thereof, wherein the method comprises the steps of: (i) generating a statement of events of the hospital environment, the statement of events related to the occurrence of at least a touch between at least a passer-by of the hospital environment with one of the items disposed in the hospital environment and, (ii) performing the cleaning action of the hospital environment (1) based on the statement of events generated.

There is also proposed a system of monitoring the cleaning of hospital environments, the hospital environment comprising at least an item disposed inside thereof, wherein the system comprises means for generating a statement of events of the hospital environment, the statement of events related to the occurrence of at least a touch between at least a passer-by of the hospital environment with one of the items disposed in the hospital environment, wherein the cleaning action of the hospital environment is performed based on the statement of events generated.

The teachings of the present invention are absorbed through the use of a plurality of sensors disposed inside the hospital environment, such as infrared sensors, contact sensors and radiofrequency sensors (RF).

SUMMARIZED DESCRIPTION OF THE DRAWINGS

Figure 6:
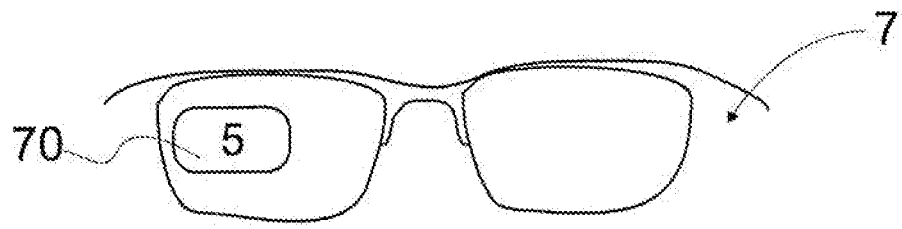
Figure 6:
Figure 6:
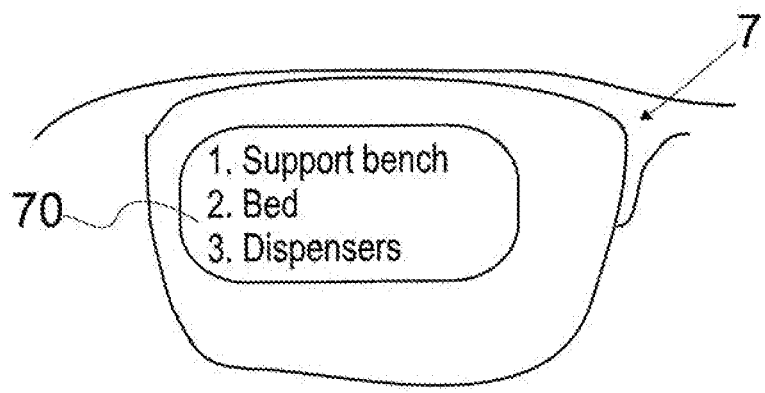
Figure 6:
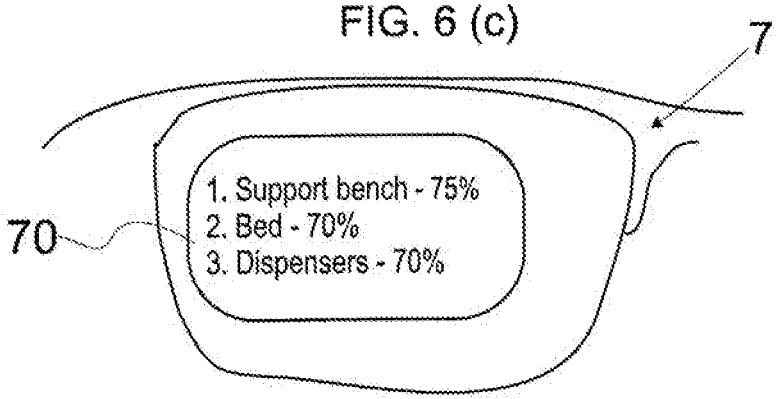
Figure 7:
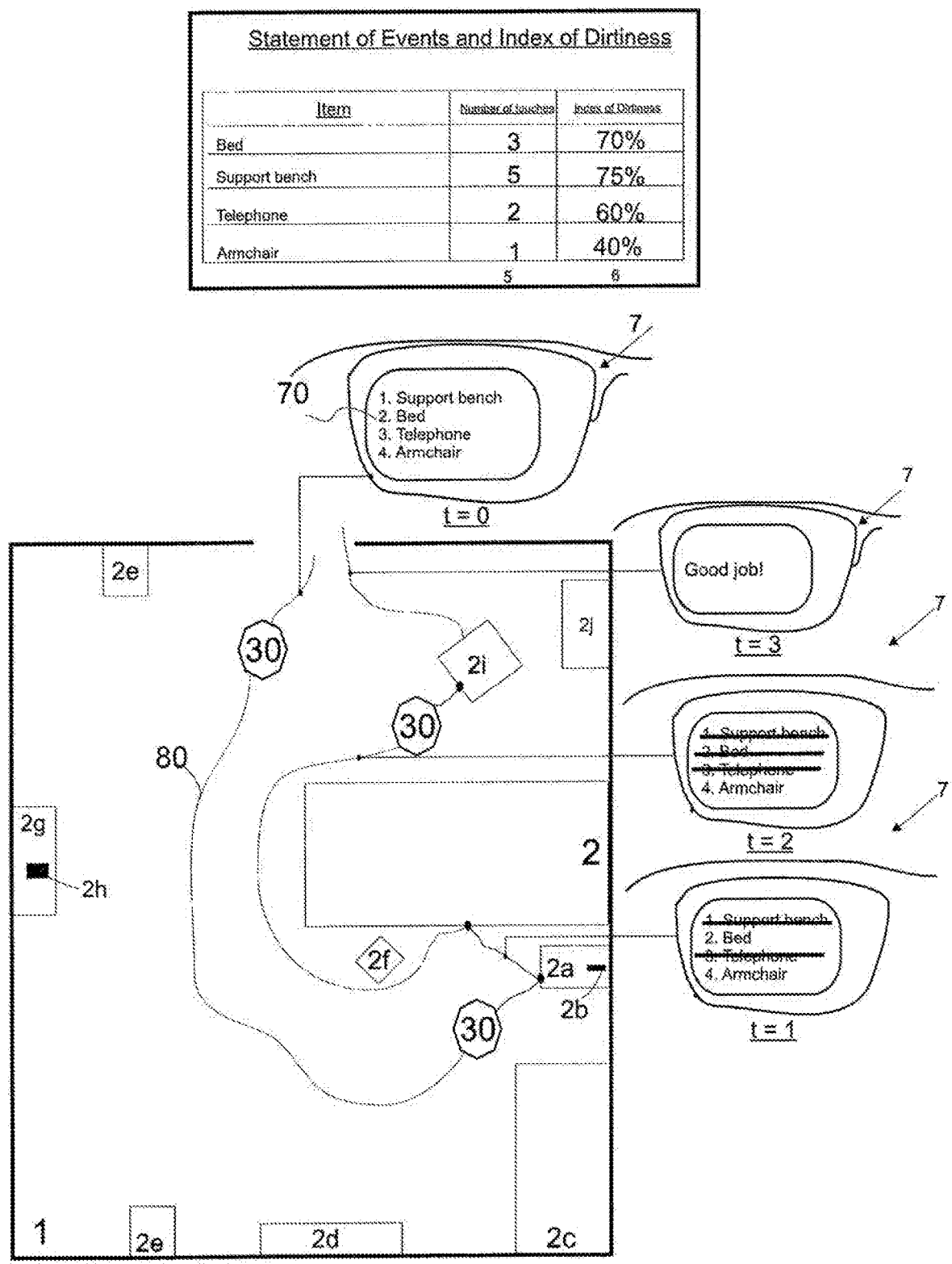
Figure 8:
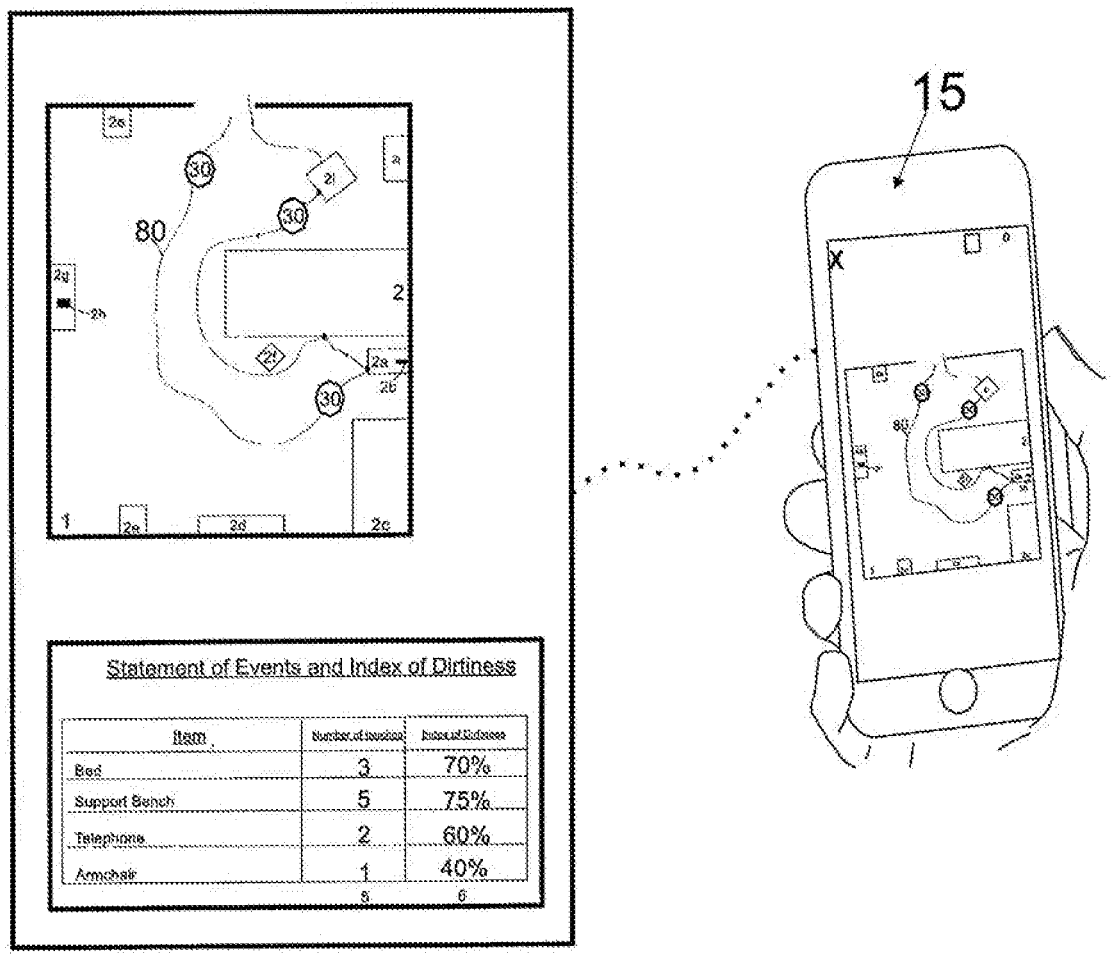
Figure 9:
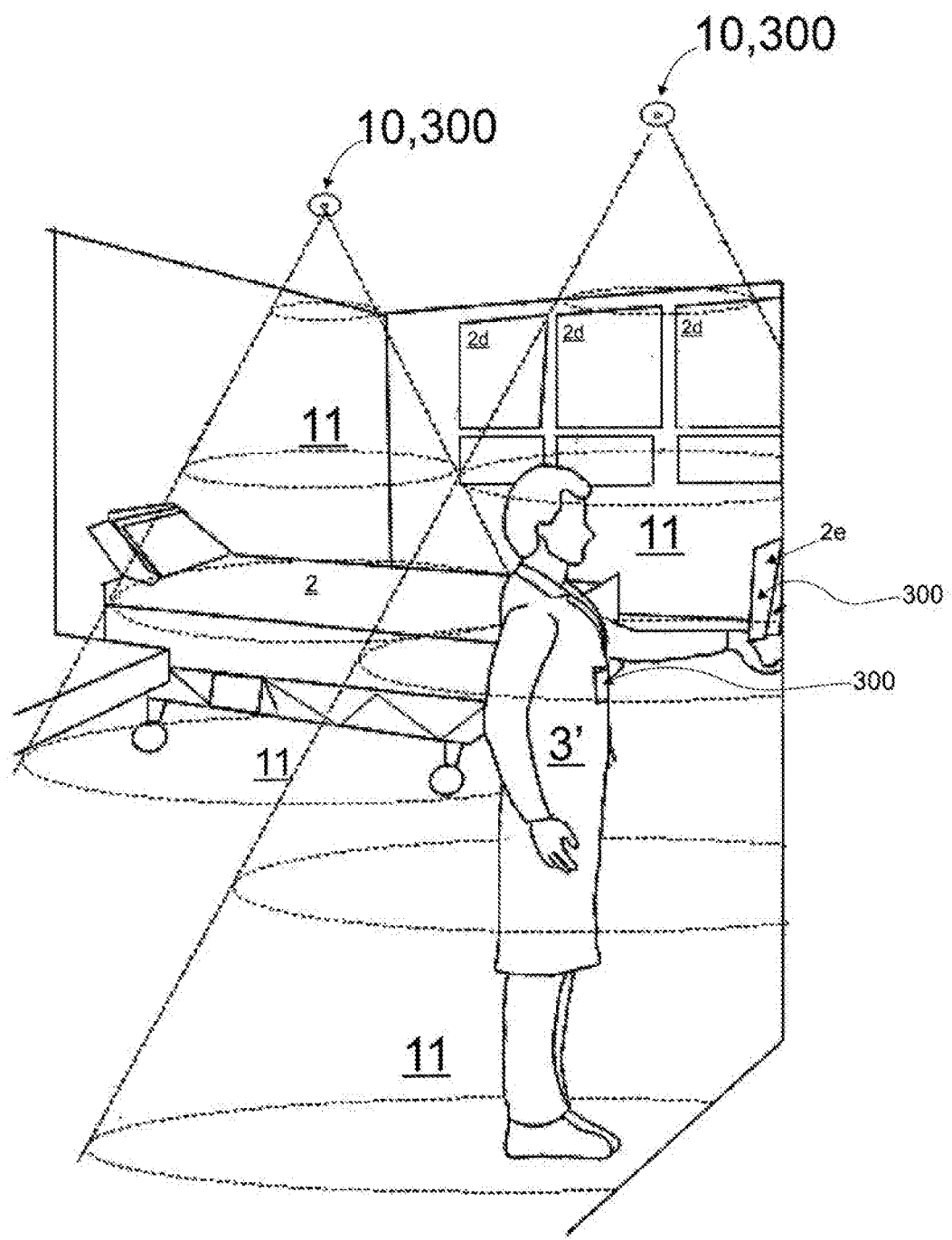
Figure 10:
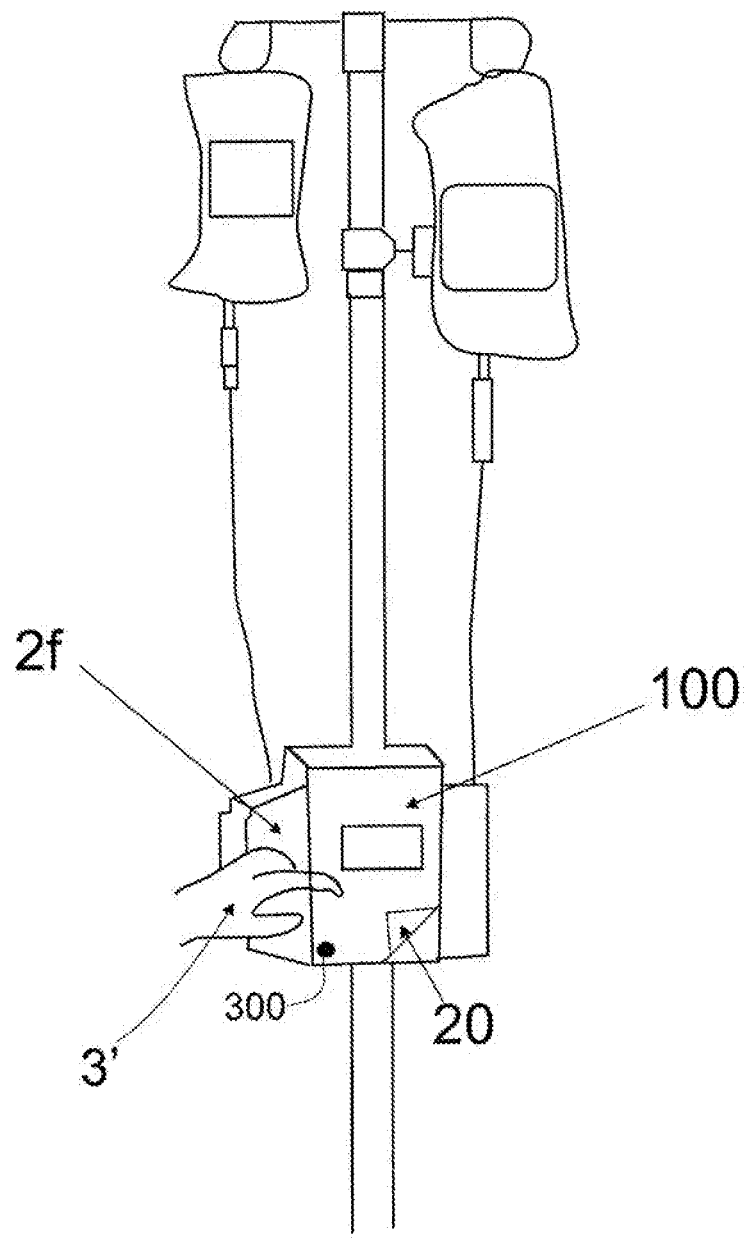

The present invention will now be described in further detail based on an example of execution represented in the drawings. The figures show:

FIG. 1—is a representation of the hospital environment capable of absorbing the teachings proposed in the present invention;

FIG. 2—is a representation of the statement of events generated based on the teachings proposed in the present invention;

FIG. 3—is an additional representation of the statement of events generated based on the teachings proposed in the present invention, indicating a consolidated statement of events;

FIG. 4—is an additional representation of the statement of events generated based on the teachings proposed in the present invention, indicating a detailed statement of events;

FIG. 5—is a representation of the dirtiness index generated based on the teachings proposed in the present invention;

FIG. 6—is a representation of a modality of the indicating element that is part of the system of monitoring the cleaning of hospital environments proposed in the present invention, wherein FIG. 6(*a*) illustrates the indication of the statement of events, FIG. 6(*b*) illustrates the indication of the dirtiness index, FIG. 6(*c*) illustrates the indication of the items to be considered in the cleaning action and FIG. 6(*d*) illustrates the items to be considered in the cleaning action jointly with the dirtiness index of said items;

FIG. 7—is a representation of the cleaning action performed in a hospital environment considering the teachings of the present invention;

FIG. 8—is a representation relating to the possibility that the indicating element may communicate with a remote device;

FIG. 9—is a representation of a hospital environment capable of absorbing the teachings of the present invention, also indicating the infrared sensors disposed inside said hospital environment; and FIG. 10—is a representation of a contact sensor associated to an item disposed inside the hospital environment.

DETAILED DESCRIPTION OF THE DRAWINGS

Initially in reference to FIG. 1, the present invention refers to a method of monitoring the cleaning of hospital environments. In this arrangement, the reference to hospital environments 1 should be understood to be a bedroom of a certain hospital.

Further, said hospital environment 1 is used to accommodate a certain patient, regardless of the period and reason for accommodation (surgery, rest, treatment, among others).

It is emphasized that the term hospital environment 1 should not necessarily relate to a bedroom of a hospital, such that any health unit, such as clinics, offices, infirmaries, surgery centers and first aid units shall also be understood as having hospital environments 1.

In general terms, and for improved understanding of the invention, the hospital environment 1 shall be understood as any place, in a health unit, or treatment unit, or accompanying unit, wherein the patient may be accommodated, either for long or short periods of time.

Thus, preferably considering the hospital environment 1 as a bedroom of a certain hospital, such as illustrated in FIG. 1, said hospital environment 1 comprises a plurality of items 2, 2*a*, 2*b*, 2*c*, 2*d*, 2*e*, 2*f*, 2*g*, 2*h*, 2*i*, 2*j* disposed therein.

More specifically, items 2, 2*a*, 2*b*, 2*c*, 2*d*, 2*e*, 2*f*, 2*g*, 2*h*, 2*i*, 2*j* shall be understood to be elements disposed inside the hospital environment 1, be they items of furniture, medical equipment, dispensers of aseptic substance, telephones, television sets, items of decoration, structural items, among others.

Preferably, any element disposed inside the hospital bedroom 1 can be considered as one of items 2, 2*a*, 2*b*, 2*c*, 2*d*, 2e, 2f, 2g, 2h, 2i, 2j. Thus, and considering this preferred modality of the present invention illustrated in FIG. 1, said hospital environment 1 comprises a bed for accommodating the patient 2, a support bench 2a with telephone 2b, a bed/couch for a companion (visitor) 2c, windows 2d, dispensers of alcohol gel 2e, an infusion pump 2f, a bench 2g for television set 2h, an armchair 2i and nursing bench 2j for handling the medicines.

Obviously, the reference to items 2, 2a, 2b, 2c, 2d, 2e, 2f, 2g, 2h, 2i, 2j should not be considered as a limitative characteristic of the present invention, such that, as already mentioned, said items can be considered as any element disposed inside the hospital environment 1.

Additionally, it will be noted throughout this specification that references are made to a passer-by 3, 3', 3", 30 of the hospital environment 1.

In this sense, said reference should be understood to be any person moving inside the hospital environment 1 or accommodated therein.

Thus, the passer-by 3, 3', 3", 30 of the hospital environment 1 can be understood to be doctors, nurses, visitors, companions, outsourced professionals (such as cleaning professionals), professionals hired by the hospital, the patient accommodated in the bed, among others.

Basically, any person inside the hospital environment 1 (regardless of the time period) should be understood to be a passer-by 3, 3', 3", 30 therein.

Thus, and in reference to FIGS. 1 and 7, the passer-by 3 can be understood to be the patient accommodated in the hospital environment 1, the passer-by 3' as the professional doctor, the passer-by 3" as the patient's companion and the passer-by 30 as the professional in charge of cleaning of the hospital environment 1.

In this arrangement, and in reference to FIGS. 1 and 2, the method of monitoring the cleaning of the hospital environment comprises the step of generating a statement of events 5 of the hospital environment 1, wherein the statement of events 5 is related to the occurrence of at least a touch between at least a passer-by 3, 3', 3", 30 of the hospital environment 1 with one of items 2, 2a, 2b, 2c, 2d, 2e, 2f, 2g, 2h, 2i and 2j.

Thus, the statement of events 5 refers to a statement identifying each of items 2, 2a, 2b, 2c, 2d, 2e, 2f, 2g, 2h, 2i and 2j disposed inside the hospital environment 1 and also indicates whether a touch (physical contact) occurred between one of the passers-by 3, 3', 3", 30 and items 2, 2a, 2b, 2c, 2d, 2e, 2f, 2g, 2h, 2i and 2j.

Accordingly, a representation of the statement of events 5 may be generated, for example, for the management of the hospital environment, wherein each of items 2, 2a, 2b, 2c, 2d, 2e, 2f, 2g, 2h, 2i and 2j is displayed as well as the quantity of touches occurred between one of the passers-by 3, 3', 3", 30 and the item in question.

Additionally, a consolidated statement of events 5' for all the passers-by 3, 3' and 3", 30 of the hospital environment can be generated, indicating the quantity of touches between them and items 2, 2a, 2b, 2c, 2d, 2e, 2f, 2g, 2h, 2i and 2j, as represented in FIG. 3.

Moreover, a detailed statement of events 5" may be generated, discriminating each of the touches by a certain passer-by considering one of the (or all the) items 2, 2a, 2b, 2c, 2d, 2e, 2f, 2g, 2h, 2i and 2j of the hospital environment 1.

Accordingly, and in reference to FIG. 4, the detailed statement of events 5" may indicate the total number of touches of the passer-by 3' (professional doctor) and may also discriminate the day and the time of occurrence of each of these touch episodes 5a, 5b and 5c in the items 2 (bed) and dispensers 2e. Additionally, the duration of each touch episode can be displayed in the statement of events 5", thus indicating whether the touch occurred for a short (such as a bump) or long period of time. Obviously, a reference period of time can be defined by the user.

It is emphasized that the representation form of the statements of events 5, 5' and 5" respectively displayed in FIGS. 2, 3 and 4 does not constitute a limitative characteristic of the present invention.

Generally speaking, the statement of events 5, 5' and 5" should be understood as any form of indication of the occurrence of a touch (physical contact) between a passer-by 3, 3', 3", 30 and an item of the hospital environment, wherein said statement of events 5, 5' and 5" will subsequently be used as a basis for performing the cleaning action of the hospital environment 1, as better described ahead.

Accordingly, the statement of events 5 (and the consolidated statement of events 5' and the detailed statement of events 5") may be generated considering a pre-set time period, such as the patient's hospitalization period 3 in the hospital environment 1.

Thus, when the patient 3 leaves the environment 1 and the need arises for terminal cleaning (cleaning action), the information contained in at least one of the statements of events 5, 5' and 5" can be used so as to boost the efficiency of the cleaning.

More specifically, the professional assigned to carry out the cleaning of the hospital environment 1 will consider the information available in the statement of events 5, 5' and 5" so as to perform the cleaning action of the environment 1.

Accordingly, it is considered that items 2, 2a, 2b, 2c, 2d, 2e, 2f, 2g, 2h, 2i and 2j are targets of the greatest quantity of touches and are more likely to accumulate bacteria, so the cleaning action can be intensified and performed with greater care at these points (items), whereby increasing the efficiency thereof and preventing the occurrence of contamination.

Accordingly, the statement of events 5,5',5" indicates which areas are most at risk of contamination ('hot spots'), thus allowing the cleaning to be performed to place greater emphasis on these areas of risk.

Moreover, the method of monitoring the cleaning of hospital environments proposed in the present invention further comprises the step of generating a dirtiness index 6 based on the statements of events 5, 5', 5" generated. More specifically, the dirtiness index 6 refers to an indication listing the occurrence of touches on a certain item with the degree of dirtiness of the item in question. More specifically, the dirtiness index 6 takes as a basis at least the touch episodes 5a, 5b and 5c appearing in the statement of events 5,5',5".

Thus, and should the management of the hospital environment 1 so wish, it may establish that the greater the number of touches detected on a certain item 2, 2a, 2b, 2c, 2d, 2e, 2f, 2g, 2h, 2i, 2j, the greater the dirtiness index 6 obtained. In a non-limitative arrangement, the dirtiness index 6 is indicated on a percentage scale, wherein 0% tends to indicate an item where no touch occurred and 100% indicates an item where a large quantity of touches occurred, as represented in FIG. 5. Further, the dirtiness index 6 may be linked to the duration of the touch episode 5a, 5b, 5c detected, where a touch of longer duration tends to provide a greater increment of the dirtiness index 6.

Obviously, it is up to the user of the proposed method to define the number of touches acceptable for each of the items 2, 2a, 2b, 2c, 2d, 2e, 2f, 2g, 2h, 2i, 2j of the hospital environment 1. Further, an item where no touch occurred does not necessarily have a dirtiness index of 0%, since the user of the proposed method is free to attribute an initial dirtiness index 6 for a certain item, for example, if cleaning is compulsory for this item. Reference is drawn to the dirtiness index 6 of item 2h (television set), depicted in FIG. 5.

It is also emphasized that the representation of the dirtiness index 6 in a percentage scale should not be considered as a limitative characteristic of the present invention, such that any form of representation is acceptable. For example, the dirtiness index 6 can be represented using the colors green and red, indicating a clean and dirty item, respectively.

Further, the dirtiness index 6 can be indicated on a graded scale of intensity going from blue (clean item) to red (dirty item), or else represent it by text messages or any other form of indication visible to the user of the proposed method.

In a preferred modality of the present invention, at least one from among the statement of events 5, 5' and 5" and the dirtiness index 6 is indicated to a user of the method of monitoring the cleaning of hospital environments proposed in the present invention.

In an arrangement, at least one from among the statement of events 5, 5' and 5" and the dirtiness index 6 are indicated to the management of the hospital environment 1. Moreover, either the statement of events 5, 5' and 5" or the dirtiness index 6 can be indicated to the professional assigned to carry out the cleaning of the hospital environment, such as the passer-by 30 indicated in FIG. 7.

Therefore, this arrangement of the present invention enables, for example, the statement of events 5, 5' and 5" and the dirtiness index 6 to be indicated to the professional assigned to perform the terminal cleaning of the hospital environment, that is, the cleaning performed when a certain patient is discharged and the environment is prepared to receive a new occupant.

Accordingly, and contrary to current procedures, the cleaning of the hospital environment 1 will consider the places (items) having the highest dirtiness index 6, that is, those places wherein the chance of proliferation of bacteria is more likely ('hot spots').

In an arrangement, it is established that the statement of events 5, 5', 5" and the dirtiness index 6 are displayed on an indicating element 7, and this element is operable (used) by the professional 30 assigned to carry out the cleaning of the hospital environment 1.

More specifically, the indicating element 7 is used by the professional 30 during the cleaning action performed in the hospital environment 1, so the professional has access to the content of both the statement of events 5, 5', 5" and the dirtiness index 6 during cleaning.

Accordingly, the teachings of the present invention propose that the indicating element 7 signals to the cleaning professional (passer-by 30) on what item 2, 2a, 2b, 2c, 2d, 2e, 2f, 2g, 2h, 2i, 2j the cleaning action should preferably be performed, also indicating to the professional 30 the level (intensity) of the cleaning to be performed considering the quantity of touches on the item in question as well as the dirtiness index 6 thereof.

In an arrangement of the present invention and in reference to FIGS. 6 and 7, the indicating element 7 is arranged with an electronic element usable by the passer-by of the hospital environment 1. More specifically, the indicating element 7 can be arranged like any electronic apparatus suitable to be used by the passer-by 30, such as a cellphone or tablet. Further, it is proposed that the indicating element 7 be wearable by the passer-by 30 assigned to carry out the cleaning of the environment 1.

A wearable element is understood to be any element that can be used by the passer-by 30 and that is suitable for reproducing and generating at least one from among video, audio and text files. Further, and merely preferably, the indicating element 7 is suitable for connecting to the world wide web.

Preferably, the indicating element 7 should be used by the cleaning professional 30 while (at the same time in which) the cleaning action is performed, thus allowing the cleaning of the environment 1, but also the consideration of the information available in the statement of events 5, 5', 5" and/or in the dirtiness index 6. It is understood thereby that the indicating element 7 enables the simultaneous visualization of the hospital environment 1 as well as at least one from among the statement of events 5,5',5" and the dirtiness index 6.

In this arrangement, and as described previously, the indicating element 7 is preferably arranged as a watch, glasses or cellphone/tablet to be used by the passer-by 30.

More specifically, and in reference to FIGS. 6 and 7, the indicating element 7 can be understood as a pair of glasses used by the cleaning professional (passer-by 30), and this element also provides protection for the user who utilizes it, thus acting as Individual Protection Equipment. More specifically, said indicating element 7 should preferably be arranged as smart glasses, such as the already known models: Google glass, HoloLens (Microsoft), and also models by the companies Vuzix, Epson, Sony, and others. Obviously, the use of these models is a non-limitative characteristic of the present invention, alternatively, any other model of smart glasses could be used.

Accordingly, the cleaning professional 30 who makes use of the indicating element 7 will be able to visualize at least one from among the statement of events 5, 5' and 5" and the dirtiness index 6, as represented in FIGS. 6(a) and 6(b), respectively.

Moreover, the item 2, 2a, 2b, 2c, 2d, 2e, 2f, 2g, 2h, 2i, 2j to be cleaned can be indicated directly to the cleaning professional, considering the information generated in the statement of events 5, 5', 5" and/or in the dirtiness index 6. Said indication may occur by text or else by graphic means (such as figures of the item to be cleaned).

Thus, and in reference to FIGS. 5 and 6(c), the items disposed in the statement of events 5 can be indicated, starting the indication by those items where most touches occurred, that is, support bench 2a, bed 2 and dispensers 2e. Further, certain items can be indicated in addition to the dirtiness index 6 thereof, as illustrated in FIG. 6(d).

With a view to enabling the passer-by 30 to visualize both the hospital environment 1 and the information provided by the indicating element 7, it is proposed that the representation of the statement of events 5, 5', 5", of the dirtiness index 6 or of the item 2a, 2b, 2c, 2d, 2e, 2f, 2g, 2h, 2i, 2j to be cleaned be performed by way of an enhanced reality interface 70 of the indicating element 7, as represented in FIG. 6.

Thus, the passer-by 30 will perfectly be able to clean the environment 1 and use the information available in the statement of events 5, 5', 5" and dirtiness index 6.

In this sense, FIG. 7 illustrates a representation of the hospital environment 1 to be cleaned by the passer-by 30 considering the teachings of the present invention. The dotted line indicates a path 80 (path datum) performed by said passer-by 30 inside the hospital environment 1. In this representation, and as addressed previously, the passer-by 30 is understood to be a professional in charge of cleaning of said environment 1.

The statement of events 5 and the dirtiness index 6 for the environment 1 as represented in FIG. 7 is also considered, wherein the items with greater quantity of touches are highlighted: bed 2, support bench 2a, telephone 2b and armchair 2i.

Thus, in a valid arrangement, upon entering the environment 1 the passer-by 30 will visualize in the indicating element 7 the representation of the items 2, 2a, 2b and 2i to be considered in the cleaning, like the indication of the enhanced reality interface 70 displayed in instant t=0, as per FIG. 7.

Knowing that items 2, 2a, 2b and 2i are to be cleaned, the passer-by 30 moves towards the support bench 2a and the telephone 2b, and carries out the cleaning of these elements. In this instant, the indication of the enhanced reality interface 70 indicates to the passer-by that the cleaning of these items has been done, as represented in instant t=1.

Subsequently, the passer-by 30 moves towards a bed 2, performing the cleaning of this element and receiving the update of the representation of the enhanced reality interface 70, as per instant t=2.

Lastly, the passer-by 30 moves towards the armchair 2i, performing the cleaning of this element and receiving the indication on the interface 70 that the cleaning work was duly performed considering the statement of events 5 and dirtiness index 6 in question.

Obviously the representation form of the enhanced reality interface 70 indicated in instants t=0, t=1, t=2 and t=3 should not be considered as a limitative characteristic of the present invention. Further, the representation relating to the cleaning of an item could be performed indicating a fall in the dirtiness index or else passing the representation of this item on the interface 70 of the color red (dirty) to the color green (clean).

Further, it is understood that the path 80 taken by the passer-by 30 and indicated in FIG. 7 should not be considered as a limitative characteristic of the present invention, such that other items of the hospital environment 1 can be cleaned by the professional, even if this item is not explicitly represented in the indicating element 7.

For example, it is known that certain health environments have cleaning protocols comprising compulsory cleaning points (items). Accordingly, said items must be cleaned even if they have not been touched. In any case, and with the use of the concepts proposed in the present invention, certain items where the cleaning would not be performed will thereafter be cleaned based on the occurrence of touches on the item in question, whereby reducing the chance of proliferation of bacteria.

In this arrangement, the method of monitoring the cleaning of hospital environments further comprises the step of evaluating the effectiveness of the cleaning action performed in the hospital environment 1. More specifically, said evaluation considers the content available in at least one from among the statement of events 5, 5', 5", dirtiness index 6 and also the path 80 performed by the passer-by 30 inside the hospital environment 1.

Thus, an evaluation will take into account whether the cleaning performed by the passer-by 30 did in fact consider the items where the occurrence of touch was detected and displayed in the statement of events 5, 5' and 5". Additionally, the evaluation of the cleaning may also consider any other compulsory cleaning item, considering a certain cleaning protocol of the hospital environment 1.

In an arrangement, the evaluation of the cleaning considers not only the items where the occurrence of a touch was detected, but also the duration of the respective cleaning action performed on the item in question.

Thus, and such as addressed previously, the duration of the touches performed between the passers-by 3, 3' and 3" and the items of the hospital environment can be considered to be linked to the possibility of transmitting bacteria. More specifically, the duration of the touches detected may represent a contributing factor to a greater/lesser increment of the dirtiness index 6.

Thus, it can be considered that a short-lasting touch (such as a bump) between the passer-by and the item will have a lesser chance of transmitting bacteria when compared to a long-lasting touch, such as contact occurring for more than a pre-set time period (such as five seconds) between the passer-by and the item disposed in the hospital environment.

Thus, the user of the proposed method is free of indicating whether the duration of the touches will be a contributing factor for a greater increment of the dirtiness index 6. Obviously, the reference to the five-second time period should not be considered as a limitation of the present invention, such that said value can be altered by the user of the method proposed in the present invention.

Thus, an evaluation can be made as to whether the time the passer-by 30 takes to perform the cleaning of a certain item is proportional to its dirtiness index 6, that is, the higher the dirtiness index 6, the more time will be spent by the passer-by 30 to clean said item.

In a modality, and in reference to FIG. 8, the cleaning action performed by the passer-by 30 can be transmitted in real time to a remote device 15 (such as a computer, tablet and/or cellphone). Accordingly, it is suffice that the indicating element 7 comprise a video device (such as a camera), and, it is possible to use the very sensors that enable the performance of the steps proposed in the present invention, as described ahead.

Accordingly, the path 80 taken by the passer-by can be relayed in real time to hospital management for accompanying the cleaning action being carried out, enabling management to evaluate, through its remote device 15, whether the cleaning action was duly performed considering the information available in the statement of events 5,5',5" and following a protocol deemed to be acceptable by the hospital environment 1. More specifically, it is proposed that both the statement of events 5,5',5" and the dirtiness index 6 also be visualizable on the remote device 15.

Further, it is proposed that the indicating element 7 be capable of two-way communication with the remote device 15, that is, enabling any datum collected by the indicating element 7 to be relayed to the remote device 15 and thus enabling the transmission of any type of datum (voice, video, text, graph) from the remote device 15 to the indicating element 7. The form of communication of the indicating element 7 with the remote device 15 does not represent a preferred characteristic of the present invention, such that any form of communication known in the state of the art can be used (such as Wi-fi, Zigbee, Bluetooth, and others).

Accordingly, the management of the hospital environment 1 can be communicated with the passer-by 30 during the cleaning action in progress, thus indicating in enhanced reality interface 70 a warning message relating to any potential item that was not cleaned or else indicating why the cleaning action was well performed or inefficient.

It is thus understood that the teachings of the present invention are extremely beneficial for training the cleaning practices performed in the hospital environment 1, thus allowing management of the environment 1 to monitor (for example, in real time) the cleaning action performed.

In harmony with the method of monitoring the cleaning of hospital environments now proposed, the present invention also addresses a system of monitoring the cleaning of hospital environments.

Thus, and for the teachings of the present invention to be duly implemented, it is proposed that the hospital environment 1 in question comprise a plurality of sensors 10, 20, 300 disposed therein. More specifically, the use is proposed of at least one from among infrared sensors 10, contact sensors 20 and radiofrequency sensors 300.

In a fully valid arrangement, the infrared sensors 10 are capable of detecting at least a heat detection zone 11 inside the hospital environment 1. Thus, and based on each of the heat detection zones 11 of the environment 1, it is possible to track (map) the movement of a certain passer-by 3, 3', 3", 30 in the environment 1 and consequently determine whether he/she touched any of the items 2, 2a, 2b, 2c, 2d, 2e, 2f, 2g, 2h, 2i, 2j disposed in the environment 1.

Basically, the infrared sensors 10 are based on the heat emitted by the human body (passers-by) and for certain items 2, 2a, 2b, 2c, 2d, 2e, 2f, 2g, 2h, 2i, 2j disposed in the hospital environment so as to determine the occurrence of touches and consequently generate the statement of events 5, 5', 5" and dirtiness index 6 addressed previously.

In this sense, it is known that the mapping of persons (passers-by) and equipment (items) inside the hospital environment 1 is possible since the form of heat emission differs between both. More specifically, any item disposed inside the hospital environment and that is connected to a power source (plug) will emit heat, thus enabling the detection thereof by infrared sensors 10.

Thus, and considering this modality of the present invention, the infrared sensors 10 are capable of detecting the heat emitted by the bed 2 (with the patient accommodated therein), telephone 2b, bed companion 2c (with the passer-by accommodated), infusion pump 2f and television set 2h. In such items, the proposal is to use radiofrequency sensors 300, so that in combination with the infrared sensors 10, it is possible to detect and store the occurrence of physical contact with the items in question.

For the so-called cold items, that is, those that are not associated to a power source, touch detection is by the use of radiofrequency sensors 300, such as RTLS (real time locating system) type sensors. Thus, the sensors 300 should be associated to the desired items and radiofrequency sensors 300 should be disposed inside the hospital environment 1. In an arrangement, three radiofrequency sensors 300 are disposed inside the environment, thus allowing the detection of the location of the item by triangulation. The placement site of said sensors 300 in the environment does not represent the main aspect of the present invention.

In an arrangement, and in reference to FIG. 9, the hospital environment 1 should comprise a plurality of infrared sensors 10, wherein each sensor 10 will respectively define a heat detection zone 11, that is, the zone where said sensors 10 are capable of operating.

More specifically, the heat detection zone 11 should be understood to be the area of detection of the infrared sensor 10, that is, the area where the sensor 10 is capable of detecting the heat emitted by a certain person (passer-by) or equipment (item).

Preferably, the infrared sensors 10 should be disposed on the ceiling of the hospital environment 1 and such that the whole area of the environment 1 is captured by the heat detection zone 11 of each of the sensors 10. Alternatively, the arrangement of the sensors on the walls, or in any other place of the hospital environment 1 is fully acceptable. In a modality, the infrared sensors 10 and the radiofrequency sensors 300 can be accommodated in a same encasement, as illustrated in FIG. 9.

In a modality, the infrared sensors 10 are preferably arranged like an infrared camera, thus generating a standard image, such as a heat map, which enables the movement of a person (passer-by) inside the environment to be identified, and his/her interaction (through radiofrequency sensors 300) with items 2, 2a, 2b, 2c, 2d, 2e, 2f, 2g, 2h, 2i and 2j disposed in the hospital environment 1.

The use of the infrared sensors 10 provides advantages for tracking a certain passer-by or equipment inside the hospital environment, for example, using said sensors (infrared cameras) it is possible to track an individual even if he/she is not wearing an identity badge endowed with a radiofrequency sensor 300 (RF sensor).

For example, it is known that some systems proposed in the state of the art present the so-called "dependency badge", that is, said systems will only operate properly if the passer-by (doctor, visitors, nurses, physiotherapists, outsourced professionals, or any health sector professional) is using an identity badge, otherwise, the tracking will not be possible and the system will not operate properly. In said systems, there is basically communication between the identity badge (endowed with an RF sensor) and RF sensors associated to equipment.

This drawback does not occur considering the teachings of the present invention, since the tracking is obtained from the heat emitted by the human body or by a certain item, so tracking is possible even if the passer-by is not endowed with a badge and identity label.

It is emphasized that the occurrence of touch between the passer-by and the so-called "cold items" (items not associated to a power source) can also be detected even if said passer-by is not wearing an identity badge, since with the infrared sensors 10 it is possible to track the movement of the passer-by and the radiofrequency sensors 300 (associated to the items and disposed in the environment) enable knowledge of the location of the item.

Thus, it is possible to use the combination of the data obtained from the infrared sensors 10 and radiofrequency sensors 300 to determine whether the passer-by moves through an area where a certain cold item is disposed, and consequently determine whether said item was touched.

In any case, there is nothing to stop the system proposed in the present invention from using radiofrequency sensors 300 associated to the passers-by (identity badges), precisely so as to identify the passer-by (by his/her registration number) who touched a certain item, such as shown in FIG. 9.

Preferably, the infrared sensors 10 and the radiofrequency sensors 300 used in the present invention have the characteristics of the sensors described in patent application BR 10 2014 027568-1, filed by these same applicants, the specification of which is incorporated herein by reference.

In a modality, and in addition to the infrared sensors 10 and radiofrequency sensors 300, the system of monitoring the cleaning of hospital environments further comprises at least a contact sensor 20 associated to at least one of items 2, 2a, 2b, 2c, 2d, 2e, 2f, 2g, 2h, 2i, 2j disposed in the hospital environment 1.

In this arrangement, the contact sensors 20 are preferably arranged like a film endowed with a plurality of sensors (capacitive or resistive) and which is associated to a surface of item 2, 2a, 2b, 2c, 2d, 2e, 2f, 2g, 2h, 2i, 2j.

The contact sensors 20 are capable of detecting the occurrence of a touch on the surface of the item where the contact sensor 20 is disposed, as well as the duration of said touch on the surface of the item in question. For example, and in reference to FIG. 10, the placement of the contact sensor 20 on a first surface 100 of the infusion pump 2f allows detection when the passer-by 3' touched the surface 100 of said pump.

In a modality, said touch event is relayed (preferably via radiofrequency) to one of the radiofrequency sensors 300 disposed inside the hospital environment 1.

It is emphasized that the description of the item as an infusion pump 2f should not be considered as a limitative characteristic of the present invention, such that the contact sensor 20 could be disposed on any other item of the hospital environment 1, be it one of the items 2a, 2b, 2c, 2d, 2e, 2f, 2g, 2h, 2i, 2j or any other element disposed inside the hospital environment 1.

Thus, and even if not indicated in the figures of the present application, the contact sensor 20 could be disposed on any other place of the hospital environment 1, such as monitors, items of furniture and of decoration, switches, faucets, or any other equipment/portion where it is desirable to verify the occurrence of a contact (touch). The same applies to the radiofrequency sensors 300.

Preferably, the contact sensors 20 used in the system proposed in the present invention have the characteristics of the contact sensors described in application BR 10 2016 027362-5, filed by these same applicants, the specification of which is incorporated herein by reference.

Thus, based on the infrared sensors 10, contact sensors 20 and radiofrequency sensors 300 described previously, it is possible to carry out the functionalities proposed in the present invention.

More specifically, the infrared sensors 10, contact sensors 20 and sensors RF 300 enable the passer-by 3, 3', 3" and 30 inside the hospital environment 1 to be tracked and consequently the physical contact events (touch) to be detected, so as to generate at least one from among the statement of events 5, the consolidated statement of events 5' and the detailed statement of events 5".

Thus, based on the generation of the statement of events 5, 5' and 5", it is also possible to generate the dirtiness index 6, such as addressed above.

Similarly, an efficiency evaluation of the cleaning action performed in the hospital environment 1 also occurs by way of infrared sensors 10, contact sensors 20 and radiofrequency sensors 300, as it is possible to track the movement of the passer-by 30 in charge of cleaning and to evaluate whether he/she went to the items disposed in the statement of events 5, 5' and 5". Further, by way of the contact sensors 20, infrared sensors 10 and radiofrequency sensors 300, it is possible to establish whether the passer-by 30 effectively touched the item where cleaning should be performed, also identifying the time duration of the respective touch and thereby determining whether said item was effectively cleaned in accordance with its dirtiness index 6.

In a valid modality of the present invention, it is proposed that after the cleaning action performed by the passer-by 30, the hospital environment 1 may also receive sanitizing equipment that operates by ultraviolet (UV sanitizing equipment), such as a sanitizing robot.

In this arrangement, it is possible to establish based on the statement of events 5,5',5" and of the cleaning action performed by the passer-by 30 in which places the UV sanitizing equipment should operate, what power it should emit for cleaning the hospital environment 1 and the length of stay thereof in each place. In an arrangement, the system proposed in the present invention may automatically determine in which place the UV equipment should be positioned for the 'hot spots' to be reached. This position indication is possible since the arrangement of the items inside the hospital environment 1 is known. The positioning of the UV equipment can be performed directly by the user of the system, or remotely, by communication via radiofrequency.

Further, and through the heat emitted by the UV sanitizing equipment, it is possible to track whether the movement of this equipment considered the items disposed either in the statement of events 5, 5', 5" or the dirtiness index 6 (evaluating whether the placement site of the sanitizing equipment was adequate, considering the items that should be cleaned). Moreover, the manager of the hospital environment 1 is able to visualize, remotely, the movement of the UV sanitizing equipment inside the environment 1, similar to that illustrated in FIG. 9.

It is also possible, by any communication interface known in the state of the art, such as Wi-Fi, Bluetooth, Zigbee or radiofrequency, to indicate (remotely) to the UV sanitizing equipment at which place of the environment 1 the cleaning should be carried out, duly positioning the equipment in this place. In a modality, said indication may occur by providing the geometric coordinates of the hospital environment 1 (through knowledge of the arrangement of the items inside the environment 1 and the distance between them), indicating where the UV sanitizing equipment should be placed, also indicating the power where it should be operated and the operating time period.

Further, and if the UV equipment comprises said functionality, it is possible to control (operate) it remotely, moving it to the desired place, making use of the infrared sensors 10 (infrared cameras) to do so.

Additionally, the UV equipment may be used only in those places/items where the cleaning action performed by the passer-by 30 was performed inefficiently and/or was not performed. Accordingly, the operating time of the UV equipment is streamlined, and consequently the hospital environment 1 (bedroom) is freed up more quickly. Thus, the use of the UV equipment becomes more assertive, as opposed to empirical, which is what currently happens.

In a non-limiting modality, it is proposed that the UV sanitizing equipment be used in cycles that may vary from 15 to 35 minutes. Further, it is possible to use said equipment in three cycles from 7 to 10 minutes, altering the position of the equipment between each cycle.

Thus, the teachings of the present invention propose a method and a system of monitoring the cleaning of hospital environments based on the areas of risk ('hot spots') in the hospital environment, wherein areas of risk is understood to be the items where the chance of proliferation of bacteria is greater.

Accordingly, and based on sensors disposed in the hospital environment, any items of the hospital environment touched by a passer-by are detected, so the cleaning action to be performed is based on practical data detected in the environment, and not just a protocol previously known and used for all bedrooms of a hospital environment.

It is thus emphasized that the teachings of the present invention provide a dynamic method and system, that is, each hospital environment will receive a certain cleaning action based on touch events occurring in that environment.

Moreover, the proposal to use the indicating element enables a visualization of the items to be cleaned, and also permits real-time monitoring of the cleaning action, which ultimately increases the efficiency thereof.

Further, and should it be in the interest of hospital management, after the cleaning action performed in the hospital environment, it is also possible to use sanitizing equipment that operates by ultraviolet (UV), such as a sanitizing robot. This constitutes a compliment to the cleaning action performed by the passer-by, or the cleaning of a place/item that has potentially not been cleaned by the passer-by.

Thus, there is proposed a method and system of multi-layered cleaning, that is, a first layer wherein the points of greatest occurrence of touches are detected ('hot spots'), a second layer wherein the cleaning action is performed based on the touch points detected in the first layer and, lastly, a third layer, capable of complementing the cleaning action and making use, for example, of a sanitizing robot. Obviously, it is emphasized that implementing the proposal set out in the third layer is not a compulsory stage of the present invention.

Further, it is underlined that the reference to the cleaning action such as the performance of the terminal cleaning of the hospital environment should not be considered as a limitative characteristic of the present invention, such that the teachings of the present invention could be used in any cleaning action (act of cleaning) to be performed in the hospital environment and/or in the items disposed therein. For example, and in a non-limiting way, the teachings of the present invention can be absorbed for carrying out and monitoring the concurrent cleaning performed in hospital environments, that is, the cleaning action which is performed daily in the hospital environment. In short, any cleaning action (act of cleaning) of a hospital environment may absorb the teachings now proposed.

Lastly, it is underscored that the reference to items 2, 2a, 2b, 2c, 2d, 2e, 2f, 2g, 2h, 2i, 2j should not be considered as a limitation of the present invention, such that the teachings now proposed can be applied to any element/item/equipment/point disposed in the hospital environment, such as the grating and the lower portion of the bed, any type of table disposed in the hospital environment, floor portions of the hospital environment, cooling equipment, among others.

Moreover, it is emphasized that the description of the indicating element 7 as smart glasses does not constitute a limitative characteristic of the present invention, such that any other electronic equipment could be used, such as a cellphone/tablet, television sets, watches, among others.

Further, and in reference to the dirtiness index 6, it is emphasized that it can be updated in real time as the touch events occur in the hospital environment, said index indicating for a plurality of hospital environments 1 of a hospital. Said index 6 may be shown to hospital management, thus allowing real-time visualization of which items have a greater potential for bacteria proliferation.

There is thus described a method and a system of monitoring the cleaning of hospital environments.

Having described an example of a preferred embodiment, it should be understood that the scope of the present invention encompasses other possible variations, being limited solely by the content of the accompanying claims, potential equivalents being included therein.

The invention claimed is:

1. A method of monitoring the cleaning of a hospital environment, the hospital environment comprising at least an item disposed inside thereof, wherein the method comprises the steps of:
    disposing a plurality of sensors within the hospital environment;
    detecting, using at least one of the plurality of sensors, a quantity of touches occurred between a passer-by and the at least one item disposed in the hospital environment, and determining a time duration for each of said touches;
    generating a dirtiness index for the at least one item disposed in the hospital environment, the dirtiness index being determined based on the quantity of the touches between the passer-by and the at least one item disposed in the hospital environment and on the time duration for each of said touches;
    generating a statement of events indicating the touches detected between the passer-by and the at least one item disposed in the hospital environment; and
    performing a cleaning action in the hospital environment based on the statement of events generated and the dirtiness index generated for said item.

2. The method as claimed in claim 1, further comprising, during said step of performing the cleaning action:
    displaying, using an indicating element, said statement of events to a cleaning professional.

3. The method as claimed in claim 2, wherein the step of displaying said statement of events comprises: representing the statement of events in the indicating element by way of an enhanced reality interface.

4. The method as claimed in claim 3, wherein the indicating element provides to the passer-by a simultaneous visualization of simultaneously displays to the cleaning professional the hospital environment and the enhanced reality interface.

5. The method as claimed in claim 4, wherein the indicating element is wearable by the professional.

6. The method as claimed in claim 5, further comprising a step of evaluating the effectiveness of the cleaning action performed in the hospital environment, said step comprising determining at least one from among:
    a quantity of touches occurred between the cleaning professional and the at least one item disposed in the hospital environment,
    a time duration for each of the touches occurred between the cleaning professional and the at least one item disposed in the hospital environment, and
    a path data of the cleaning professional inside the hospital environment during the performance of the cleaning action, the path data comprising data related to the path followed by the cleaning professional during the performance of the cleaning action.

7. The method as claimed in claim 3, further comprising:
    sending the path data to a remote device, the remote device disposed remotely to the indicating element.

8. The method as claimed in claim 4, further comprising:
    enabling bidirectional data traffic between the indicating element and the remote device.

9. The method as claimed in claim 5, further comprising, after the step of performing the cleaning action:
    disposing a UV sanitizing equipment in the hospital environment, wherein a placement of the UV sanitizing equipment is chosen based on the statement of events.

10. The method as claimed in claim 6, further comprising the steps of:
    defining a placement site of the UV sanitizing equipment in the hospital environment based on the statement of events,
    defining an operating power of the UV sanitizing equipment based on the statement of events and,
    defining an operating time of the UV sanitizing equipment based on the statement of events.

11. The method as claimed in claim 1, wherein said steps of detecting a quantity of touches occurred between a passer-by and the at least one item disposed in the hospital environment, and determining a time duration for each of said touches are performed using a plurality of sensors disposed in the hospital environment, wherein the plurality of sensors is selected among infrared sensors, contact sensors and/or radiofrequency sensors.

* * * * *